US012741057B2

(12) United States Patent
Haaparanta et al.

(10) Patent No.: US 12,741,057 B2
(45) Date of Patent: Sep. 22, 2026

(54) METHOD FOR PREPARING A THREE-DIMENSIONAL SCAFFOLD FOR MEDICAL USE

(71) Applicant: ASKEL HEATHCARE LTD., Helsinki (FI)

(72) Inventors: Anne-Marie Haaparanta, Kangasala (FI); Virpi Muhonen, Helsinki (FI); Laura Johansson, Tampere (FI); Kaisa Laine, Tampere (FI)

(73) Assignee: ASKEL HEALTHCARE LTD., Helsinki (FI)

( * ) Notice: Subject to any disclaimer, the term of this patent is extended or adjusted under 35 U.S.C. 154(b) by 223 days.

(21) Appl. No.: 18/049,464

(22) Filed: Oct. 25, 2022

(65) Prior Publication Data

US 2023/0109982 A1 Apr. 13, 2023

Related U.S. Application Data

(63) Continuation of application No. PCT/EP2021/061222, filed on Apr. 29, 2021.

(30) Foreign Application Priority Data

May 1, 2020 (DK) .................................. 202000521

(51) Int. Cl.

*A61L 27/24* (2006.01)
*A61L 2/081* (2026.01)
*A61L 27/48* (2006.01)
*A61L 103/05* (2026.01)

(52) U.S. Cl.

CPC ............... *A61L 27/24* (2013.01); *A61L 2/081* (2013.01); *A61L 27/48* (2013.01); *A61L 2103/05* (2026.01)

(58) Field of Classification Search

None

See application file for complete search history.

(56) References Cited

U.S. PATENT DOCUMENTS

| | | | |
|---|---|---|---|
| 3,636,956 A | 1/1972 | Schneider | |
| 10,379,106 B2 | 8/2019 | Gasik et al. | |
| 11,173,130 B2 * | 11/2021 | Ilios | A61K 47/32 |
| 2003/0008395 A1 * | 1/2003 | Holy | A61L 27/3847 435/396 |
| 2006/0252981 A1 | 11/2006 | Matsuda et al. | |
| 2009/0035858 A1 | 2/2009 | Bayon et al. | |
| 2011/0262486 A1 | 10/2011 | Tsai et al. | |
| 2017/0273775 A1 | 9/2017 | Rocco et al. | |
| 2022/0054703 A1 * | 2/2022 | Muhonen | A61L 27/18 |

FOREIGN PATENT DOCUMENTS

| | | |
|---|---|---|
| CN | 102872480 A | 1/2013 |
| CN | 107050520 A | 8/2017 |
| CN | 109675119 A | 4/2019 |
| WO | WO95/22301 A1 | 8/1995 |
| WO | WO2006/124988 A2 | 11/2006 |
| WO | WO2016/042211 A1 | 3/2016 |
| WO | WO2018/017549 A1 | 1/2018 |

OTHER PUBLICATIONS

Dai et al.,"Sterilization techniques for biodegradable scaffolds in tissue engineering applications", Journal of Tissue Engineering, vol. 7, pp. 1-13. (Year: 2016).*

Muhonen, V., et al., "Articular Cartilage Repair With Recombinant Human Type II Collagen/Polyactide Scaffold in a Preliminary Porcine Study," J. Ortho. Res. 2016;745-753.

International Search Report and Written Opinion for PCT Patent App. No. PCT/EP2021/061222 (Jul. 30, 2021).

International Preliminary Report on Patentablity for PCT Patent App. No. PCT/EP2021/061222 (Jan. 10, 2022).

Haaparanta, A.-M., et al., "Preparation and characterization of collagen/PLA, chitosan/PLA, and collagen/chitiosan/PLA hybrid scaffolds for cartilage tissue engineering," J. Mater. Sci.: Mater. Med. 2014;25:1129-1136.

Search Report from Danish Patent App. No. PA 2020 00521 (Oct. 15, 2020).

Gasik, M., et al., "The Importance of Controlled Mismatch of Biomechanical Compliances of Implantable Scaffolds and Native Tissue for Articular Cartilage Regeneration," Frontiers Bioeng. Biotechnol. 2018, vol. 6, Article 187, 11 pp.

English language translation of Office Action from Japanese Patent App. No. 2022-566053 (May 21, 2024).

Office Action from Korean Patent App. No. 10-2022-7041761 (Sep. 24, 2024).

Mohiti-Asli, M., et al., "Ibuprofen loaded PLA nanfibrous scaffolds increase proliferation of human skin cells in vitro and promote healing of full thickness incision wounds in vivo," J. Biomed. Mat. Res. B Appl. Biomater. 2017;105B:327-339.

Tambe, N., et al., "Novel genipin-collagen immobilization of polylactic acid (PLA) fibers for use as tissue engineering scaffolds," J. Biomed. Mater. Res. B Appl. Biomater. 2015;103B:1188-1197.

Faraj, K. A., et al., "The Effect of Ethylene Oxide Sterilisation, Beta Irradiation and Gamma Irradiation on Collagen Fibril-Based Scaffolds," Tissue Eng. Regenerative Med. 2011;8(5):460-470.

Online Browsing Platform (OSP), "ISO 11137, excerpt: Sterilisation of healthcare products", cited Dec. 16, 2024, 1 pg.

Sahoo, S., et al., "Developmenthybrid polymer scaffolds for potential applications in ligament and tendon tissue engineering," Biomed. Mater. 2007;2:169-173.

(Continued)

*Primary Examiner* — Anand U Desai

(74) *Attorney, Agent, or Firm* — Cermak & McGowan LLP; Malcolm K. McGowan

(57) ABSTRACT

A method for preparing a sterilized scaffold for medical use, the method comprising the steps of:

i) Loading collagen to a fiber mesh containing fibers of polylactide polymer or copolymer (commonly denoted PLA) to obtain a PLA-collagen scaffold, ii) Drying the PLA-collagen scaffold obtained from step i), iii) Sterilizing the PLA-collagen scaffold obtained from the drying step ii) to obtain the sterilized scaffold.

The sterilized scaffold obtained has improved biomechanical properties compared with an unsterilized scaffold.

19 Claims, 5 Drawing Sheets

(56) References Cited

OTHER PUBLICATIONS

Urita, Y., et al., "Evaluation of diaphragmatic hernia repair using PLGA mesh-collagen sponge hybrid scaffold: an experimental study in a rat model," Pediatric. Surg. Int. 2008;24:1041-1045.

Wang, X., et al., "Fabrication and characterization of poly(L-lactide-co-glycolide) knitted mesh-reinforced collagen-chitosan hybrid scaffolds for dermal tissue engineering," J. Mech. Beh. Biomed. Mat. 2012;8:204-0215.

Zurina, I. M., et al., "2D/3D buccal epithelial cell self-assembling as a tool for cell phenotype maintenance and fabrication of multilayered epithelial linings in vitro," Biomed. Mater. 2018; 13:12 pp.

Office Action for Indian Patent App. No. 202227062841 dated Mar. 17, 2026.

* cited by examiner

METHOD FOR PREPARING A THREE-DIMENSIONAL SCAFFOLD FOR MEDICAL USE

FIELD OF THE INVENTION

The present invention relates to a method for preparing a three-dimensional scaffold for use as biomaterial in medicine or cosmetics. The scaffold is composed of a polylactide or polylactic acid polymer or copolymer (commonly denoted PLA) and a collagen. The method involves steps that enable the preparation of a scaffold with desired properties regarding i) a set of biomechanical features, ii) stability, and iii) purity. Moreover, the method does not comprise steps that may lead to significant degradation of ingredients used, i.e. PLA and collagen, or steps that may lead to significant degradation of the PLA-collagen scaffold obtained. Furthermore, a sterilization step has unexpectedly been shown to impart certain biomechanical properties to the scaffold.

BACKGROUND OF THE INVENTION

The need to develop tissue substitutes and regeneration platforms is one of the most demanding and challenging applications in modern tissue engineering. Three-dimensional biomaterial structures (scaffolds) are highly desirable, matching the biomechanical properties of the tissue and closely mimicking in vivo behaviour (facilitating cell adhesion, growth, and tissue formation). Such biomaterials typically assist the body to rebuild the damaged tissue and eventually, they minimize associated pain and healing time. Especially for tissues where load-adapting properties are necessary, the combined static and dynamic biomechanical properties of the scaffolds are crucial for the final success of the treatment. Any progress in the development of scaffolds should ensure a high correlation between in vitro conditions and expected in vivo tissue regeneration. The non-toxic biodegradation of the scaffold should gradually transfer the stress to the new growing tissue over an appropriate time period. The synergetic effect of correct mechanical stimulation is greatly dependent on the scaffolding material, its intended biological environment and cell presence.

One of the most challenging applications of biomedical scaffolds is the articular cartilage (AC) repair. The damage and degradation of AC are not only progressing with age, obesity, or systemic diseases, but also in the young and active population due to physical causes, such as injury. If untreated, these defects may progress toward osteoarthritis (OA), affecting over 240 million people worldwide. Natural wound healing, in full-thickness defects of cartilage, often leads to the formation of fibrocartilage, which is functionally and biomechanically inferior to the original hyaline cartilage, making the tissue more prone to further deterioration and osteoarthritic changes of the joint. Initiated vicious cycle ultimately will call for a total or partial joint replacement. Therefore, biomaterial solutions with ability to regenerate cartilage are highly desirable to treat cartilage lesions at early stages before manifestation of OA.

Clinically used biomaterials include various naturally derived and synthetic materials. The advantage of natural materials is their natural feasibility for the purpose, although application of animal derived materials (xenografts) contains certain risks, such as contamination and undesired immune response. This could be avoided by using synthetic materials not causing foreign body or hypersensitivity reactions themselves. Synthetic materials can be made biologically more advantageous and biocompatible. On the other hand, compared to the naturally derived materials, synthetic polymers are usually lacking the desired intrinsic biological cues that promote cell adhesion, proliferation and tissue recovery. However, any biomaterial is always challenging to evaluate and optimize for clinical use and for the purpose of aiming on "precise medicine" solutions. It is now widely anticipated that the present level to evaluate the mechanical function of biomaterial and tissue engineering constructs is highly insufficient.

Synthetic materials with fibrous origin are often used for AC repair applications. These scaffolds have 75-85% porosity.

The structure, functions and biomechanical behaviour of AC are very complex, highly anisotropic and time- and loading history-dependent. The articular cartilage consists of a relatively small number of chondrocytes surrounded by a multi-component matrix, which can be imaged as a composite with 70-85% water and remaining proteoglycans (proteins with glycosaminoglycans attached as a bottle-brush-like structure) and collagen. Proteoglycans and water concentration vary through the depth of the cartilage tissue.

Without blood supply and lymphatic drainage, articular cartilage stands isolated and virtually lacks the wound healing response of other connective tissues. The tissue's high exposure to biomechanical aberrations results in high incidence level of cartilage lesions. Such lesions, traumatic or due to prolonged non-physiological loading, often develop to osteoarthritis (OA). OA is the number one cause of musculoskeletal ailment worldwide, with the incidence level of 7-10% of people in western population. The estimated cost of OA in a newly diagnosed patient is $6,800 per year, thus postponing OA by 10 years leads to savings of $68,000 per patient. The expenditure for OA in EU is approximately 15-20 billion per year. While traditionally not indicated for the treatment of OA, cartilage repair has become a focus of increased interest due to its potential to alter the progression of the degenerative disease, with the hope of delaying or obviating the need for joint replacement.

In addition to significant morbidity and the potential for disablement, cartilage trauma and degeneration has major economic impacts as well. Estimating that the annual incidence of cartilage lesion is 23 per 100 000 population, there are more than 100 000 patients with a cartilage defect of the knee requiring repair treatment in the EU. The prevalence of cartilage pathologies is expected to rapidly increase in the following decades due to an aging population, as well as increased rates of obesity; the demand for knee replacements is projected to increase significantly through 2030. On the other hand, young patients with symptomatic cartilage lesions represent a challenging population due to a combination of high functional demands and limited treatment options. The aim of articular cartilage repair treatment is to restore and maintain the normal function of the joint with repair tissue architecture indistinguishable of the natural hyaline cartilage. However, current repair techniques for cartilage lesions are inadequate and need development.

After surgical repair, the biomechanical properties of the repaired site are weakened, and postoperative loading has to be reduced. Therefore, it is expected that the lack of mechanical stimulus leads to slow tissue turnover and healing; thus, the recovery time remains long. As mentioned above, biomaterial scaffolds can provide structural support to the healing lesion to allow early load bearing and, thus, enhance the healing process. A wide variety of three-dimensional scaffolds, both natural and synthetic, have been introduced for cartilage repair.

One type of scaffolds of particular interest in the present context is a scaffold made of polylactide polymer or copolymers, commonly denoted PLA. Such scaffolds have been the subject of a number of publications:

PLA scaffolds have e.g. been described in Muhonen et al., published online in Wiley Online Library DOI 10.1002/jor 23099, 2015. Gamma irradiated PLA scaffolds were immersed in a solution of recombinant human type II collagen to obtain a rhCo-PLA scaffold and this scaffold was tested in a porcine study using a membrane-induced autologous chondrocyte implantation (MACI) procedure. The results were compared with a MACI-treatment group using a commercial membrane (Chondro-Gide®) and a control group without any treatment. Both treatment groups showed improvement compared to the control group, but the difference was not statistically significant. In some of the rhCo-PLA treated lesions, the mechanical properties, as well as repair tissue structures resembled very closely the properties of healthy cartilage.

Gasik et al in Bioengineering and Biotechnology, Volume 6, November 2018, relates to sterile PLA scaffolds that were doped with a solution of recombinant human collagen III to obtain a rhCo-PLA scaffold. Two types of scaffolds were compared: PLA and rhCo-PLA scaffold. The results of biomechanical comparison of the two scaffold types showed how both collagen addition and media composition change elastic, viscoelastic and inelastic properties of the scaffolds. In this study, the analysis of the in vivo cartilage repair scores from the study of Muhonen et al. was additionally performed using BUGS—Bayesian inference Using Gibbs Sampling, a form of a Markov Chain Monte Carlo sampling. The results of using normal or Poisson distributions of the total normalized ICRS (International Cartilage Repair Society) scores show rhCo-PLA having a statistically significant higher average score (0.515) vs. 0.38 for commercial scaffold and 0.288 for spontaneous healing control group.

Salonius et al., J. Cell. Physiol. 2019, relates to cell therapy combined with biomaterial scaffolds. Experimental scaffold type used was based on recombinant human collagen-polylactide (rhCo-PLA), which was prepared by immersion of a sterile PLA scaffold into a solution of recombinant human collagen II or III. Control scaffold type was commercial Chondro-Gide® membrane produced from porcine-derived type I/111 collagen. The results showed that the type II collagen promotes mesenchymal stromal cell (MSC) proliferation, but the collagen type used in the rhCo-PLA scaffolds does not affect MSC differentiation during in vitro culture and that the chondrogenic differentiation of MSC's leads to cell hypertrophy in the rhCo-PLA scaffolds and on the commercial collagen membrane. However, it was stated that the limitations of a static cell culture have possibly affected the results, as hypertrophy is a common phenomenon in in vitro chondrogenesis of MSCs, whereas MSCs in articular cartilage defects in vivo have not shown upregulation of hypertrophic markers. In joints, the cells are under cyclic mechanical loading that provides the joint with a flux of nutrients and differentiation cues.

WO 2016/042211 (University of Helsinki et al.) relates to a three-dimensional material obtained by immersing a sterile felt of a polymer into a solution of a collagen. The polymer may be PLA. It is shown that such a scaffold has improved retainability/stiffness compared to scaffolds containing bovine type I collagen or recombinant human type II collagen. Compared with a Chondro-Gide® scaffold, which is a two-layer hydrophilic collagen type I/111 membrane extracted from pigs, a rhCo-PLA showed better performance after 4 months of healing after implantation into the right knee of a pig.

However, there is a clear need for cost-effective, safe and reliable scaffolds that have the desired properties and are still safe and sterile. Moreover, it would be advantageous if such scaffolds had a general utility not only in cartilage repair, but in medicine or cosmetics in general, including human as well as veterinarian use.

SUMMARY OF THE INVENTION

The present invention relates to a method for preparing a sterilized scaffold for medical use, the method comprising the steps of:

i) Loading collagen to a fiber mesh containing fibers of polylactide or copolymer (commonly denoted PLA) to obtain a PLA-collagen scaffold, ii) Drying the PLA-collagen scaffold obtained from step i), iii) Sterilizing the PLA-collagen scaffold obtained from the drying step ii) to obtain the sterilized scaffold.

During the preparation, measures are taken to avoid unnecessary degradation of the PLA, the collagen and the PLA-collagen scaffold. Thus, the sterilizing step of the PLA-collagen scaffold are carried out without giving any, or at least only minor, temperature-rise in the scaffold. This may be done e.g. by choice of sterilization method and/or by taking special precautions to avoid a temperature rise. Moreover, as shown in Example 3 herein, the sterilized scaffold has improved biomechanical properties compared with a non-sterilized scaffold and thereby also improved biomechanical properties compared with a scaffold prepared under aseptic conditions.

The fiber mesh used in a method of the present invention may be obtained by i) providing PLA in solid form, ii) subjecting PLA to a process whereby fibers of PLA are obtained, and iii) subjecting the obtained fibers to a process, whereby a mesh of fibers is obtained.

Fibers of PLA may be produced by known methods. In embodiments of the present invention, a suitable method to produce PLA fibers is by spinning, such as by melt spinning or electrospinning. The spinning is typically carried out by melting the PLA and subjecting the molten PLA to the spinning process, or by dissolving PLA in a suitable solvent and subjecting the PLA solution to the spinning process. The fibres obtained may be subjected to a process, whereby the fibres are contained in a mesh and such a mesh may further by subjected to a process, whereby a 3D structure is obtained; furthermore, the mesh may be subjected to a process that ensures the fibers of the mesh or its 3D structure are (is) kept together.

Different structures of the scaffold may be obtained.

1. One-dimensional (1 D) fiber structures, wherein collagen is loaded on the fiber (length and diameter of the fibers can vary)
2. Impermeable, two-dimensional (2D) substrates: the structure allows a bioactive (e.g. cells) to be included in the structure. Typically, cells are cultured in a 2D environment.
3. Three-dimensional (3D), nanoporous hydrogel scaffolds, wherein collagen is typically located on top of the hydrogel (i.e. interacting with 2D substrates with a nano-scale surface) or encapsulated inside the 3D structure (the cells have to degrade the surrounding hydrogel to move or extend processes).

4. Three-dimensional (micro-porous) scaffolds, wherein the bioactive is able to spread in three dimensions because of high porosity (typically >70%) and, depending on scaffold pore size, they can either be aligned along one-dimensional scaffold struts or attached to multiple struts and spread in three dimensions.

In the present context, the description of the scaffold is also intended to cover the sterilized scaffold.

Typically, a scaffold of the present invention has a three-dimensional structure. As described above, a three dimensional structure may further be in the form of a nanoporous hydrogel scaffold, wherein the bioactives are on top of the hydrogel or encapsulated inside the 3D structure and the surrounding hydrogel has to be degraded in order to release the bioactive, or the three dimensional structure may be in the form of a microporous scaffold, wherein bioactives are able to spread in three dimensions because of the high porosity of the scaffold.

A scaffold according to the invention may be used as such or loaded with one or more bioactive. A bioactive may be one or more cell(s), or it may be an agent that has activity in a biological environment, notably in a mammalian body. The cells to be loaded into a scaffold according to the invention may be cells intended for repairing a diseased or damaged tissue. Other bioactives may be drug substances that are suitable for alleviating pain or suitable for treating a disease in a particular tissue. It may also be a drug substance intended for systemic use, but wherein it is easy to administer the drug substance in an implant. The scaffold may be in the form of an implant or as a bandage. It may be used in medicine, such as in human medicine, as well as in veterinary medicine. A scaffold according to the invention may be used for different medical purpose, notably in connection with repair of cartilage, such as AC, or in connection with osteochondral repair. It may also be used in a treatment regime, such as e.g. in AO or the like.

Native cartilage is not porous as such, but for example, the porosity of natural bone, which contains high amounts of collagens, is in the range of 50-90%, depending on the type of the bone. A highly porous, interconnected and open pore structure is needed for tissue engineering scaffolds to ensure tissue ingrowth and the flow transport of nutrients and metabolic waste. The porosity of a material can be determined in multiple ways. For example, micro-computed tomography (microCT) analysis, image analysis (such as scanning electron microscopy or transmission electron microscopy), gas pycnometry as well as mercury and liquid extrusion porosimetry can be used. For the overall porosity, the microCT analysis is considered as the best method, as it gives reliable results on the determination of the overall porosity.

The fiber mesh used in the present method has a porous structure. The porosity of the PLA fiber mesh is about 80 to 99%, preferably being around 85 to 95%. The porosity of the scaffold with both components, the PLA fiber mesh and the collagen component, is about 70 to 99%, preferably being around 80 to 95%. The scaffold before and after sterilization has a porosity within the same ranges.

DETAILED DESCRIPTION OF THE INVENTION

As mentioned above, the present invention provides a method for preparing a sterilized scaffold. The method comprising the steps of:

i) Loading collagen to a fiber mesh containing fibers of polylactide or copolymer (commonly denoted PLA) to obtain a PLA-collagen scaffold, ii) Drying the PLA-collagen scaffold obtained from step i), iii) Sterilizing the PLA-collagen scaffold obtained from the drying step ii) to obtain the scaffold.

The method of the invention is designed to avoid any unnecessary degradation of the PLA and the collagen used, and to avoid unnecessary degradation of the fiber mesh and/or the PLA-collagen scaffold. Thus, the amount/numbers of monomers present in the starting material PLA does not significantly change during the process, so that the amount/numbers of PLA monomers in the final scaffold is close to the starting PLA material. During pre-method steps of the present invention, PLA may be subjected to elevated temperatures in order to obtain a fiber mesh containing the PLA fibers and some degradation of the raw PLA material is expected to occur e.g. during a spinning process to obtain a mesh of PLA fibers. In general, the content of monomers in the raw PLA material (before fiber formation) is very low, such as about 0.1%, and the content of monomers in the fiber mesh is typically at the most about 1%.

Analogously, only minimal degradation of collagen takes place during the manufacturing of the scaffold by a method of the present invention. The stability of the scaffold during transformation into a sterilized scaffold is ensured inter alia by avoiding temperature rises of the collagen component during manufacturing, especially during the sterilization process, and by ensuring that the sterilization method has no extensive negative effect on the biomechanical properties of the scaffold. As mentioned herein before, the sterilization process unexpectedly has positive effect on the biomechanical properties of the scaffold. Thus, the sterilization with gamma radiation at room temperature or at lower temperature imparts a more stable structure in both dry as well as wet state of the scaffold. The scaffolds become stiffer and have less variation in the biomechanical characteristics, which are advantageous in relation to approval of the scaffolds prepared.

Regarding the stability issues, PLA contains ester bonds that are susceptible to thermal, radiation and hydrolytic degradation. Collagen may also be degraded by several mechanisms including enzymatic, radiation-induced or temperature-dependent degradation.

The scaffold obtained may be used as such, or it may be loaded with bioactives, such as but not limited to cells, or with a drug substance and used as an implant. In such cases, the sterilisation of the scaffold may take place before or after loading the scaffold with a bioactive, such as but not limited to a drug substance or cells.

The method of the present invention provides a scaffold that has one or more of the following properties:

When used in implants, it should be biocompatible to support cell viability and biodegradable, so that the new tissue replaces the scaffold after time, and so that the degradation products are not harmful locally or systemically.

It should have a highly porous 3D structure with interconnected pores in order to allow cells to migrate inside the scaffold, so that they can proliferate and form new tissue.

It should have appropriate porosity for the cells to be loaded into the scaffold before use, so that the cells stay inside the scaffold, so that they can proliferate and form new tissue.

- It should have appropriate biomechanical strength for the application, e.g. for the mechanical stimuli to work well in the AC surroundings, enabling new tissue formation.
- It should not closely mimic the natural tissue that it is aiming to replace, but it should have suitable compression and decompression functionalities for the application, as well as fluid-absorption and interstitial fluid pressurization during loading and compression.
- It should have an appropriate degradation time for the application to be able to assist tissue ingrowth and subsequent forming of new tissue.

Polymers for Use in a Method of the Invention

A PLA-collagen scaffold is prepared according to the present invention. In the present context, PLA is intended to include polylactides in all stereoisomer forms including polylactide based on L-lactide, D-lactide, and polymers based on both L- and D-lactides. The ratio between the content of the L-form and the D-form may vary. Typically, PLA used in the present method contains both L—and D-forms of lactide. In respect to polylactides, the presence of D-forms in the polymer typically has impact on the time it takes for the polymer to degrade. The content of D-forms reduces the degradation time. In this manner, a PLA with desired degradation time can be designed by varying the content of L- and D-forms in the polymer. However, the content of D-forms has also an impact on the biomechanical properties of the scaffold obtained. Thus, the higher content of D-forms in the scaffold, the weaker are the biomechanical properties. It is therefore important to select a proper balance between the L- and D-forms in a polylactide for use in a method of the present invention. In general, a content of D-form is typically from about 1 to about 50% w/w such as from about 2 to about 40% w/w, from about 3 to about 35% w/w, or from about 4 to about 30% w/w. In one embodiment of the invention, the polylactide contains 96% of the L-form and 4% of the D-form; such a lactide is also denoted a 96/4 poly(L/D)lactide.

In the present context, the term PLA also includes polylactide or co-polymers, such as those formed between lactide and glycolide, poly(lactide-co-glycolide) (PLGA). The content of lactide and glycolide may vary.

The raw PLA material used to obtain a PLA fiber mesh, for use in the method of the present invention, has an inherent viscosity—determined at room temperature—from about 1.5 dl/g to about 5 dl/g, such as from about 1.5 dl/g to about 4 dl/g, from about 1.7 dl/g to about 3 dl/g, from about 1.7 dl/g to about 2.5 dl/g, or of about 1.8 dl/g, about 1.9 dl/g, about 2.0 dl/g or about 2.1 dl/g, and a max content of monomers from about 0 wt % to about 1 wt %, such as from about 0.1 wt % to at the most 1 wt %.

In the following, more details are given relating to biodegradable PLA polymers that are suitable for use in a method of the present invention.

Suitable polymers are biodegradable polymers. They may be natural or synthetic polymers. In general, synthetic bioabsorbable polymers are widely studied as tissue engineering scaffolds. Their controllable chemistry and properties, as well as their characteristic of being easily reproducible, have exceeded their use as scaffold materials. Synthetic bioabsorbable polymers can be divided into various subgroups, such as esters, orthoesters, anhydrides, carbonates and amides, depending on their functional group's susceptibility to hydrolysis. In particular, polyesters have been used in a number of clinical applications because of their ease of degradation by hydrolysis of ester linkage. Also, their degradation products are in some cases resorbed through the metabolic pathways, and they possess the potential to alter their degradation rates by tailoring their structures.

Some of the most widely and earliest studied synthetic bioabsorbable polymers used in tissue engineering are polyesters. The uniqueness of poly(α-esters) lies in their vast diversity and synthetic versatility. In the class of poly(α-esters), the poly(α-hydroxy acid)s, which include polyglycolide (PGA) and the stereoisomeric forms of polylactide (PLA), are the most widely studied polymers.

In a method of the present invention, a PLA is used. PLAs are thermoplastic, biodegradable polymers produced either by condensation polymerization from lactic acid, derived from the fermentation of sugars from carbohydrate sources, such as corn, sugarcane and tapioca or by ring-opening polymerization from lactide, the cyclic dimer of lactic acid. Because of its chiral carbon atom, lactic acid exists in two enantiomeric forms referred to as L-lactic acid (S), which occurs in the metabolism of all animals and microorganisms, and D-lactic acid (R). With condensation polymerization, only low molecular weight PLA is usually obtained. High molecular weight PLA can be obtained by ring-opening polymerization in which the polycondensation of lactic acid is followed by depolymerisation into the dehydrated cyclic dimer, lactide. The optically active lactide can be found either as D-lactide, L-lactide or as meso-lactide (D,L-lactide). In addition to the three diastereomeric structures, racemic lactide, a racemic mixture of D-lactide and L-lactide also exists. The structure and composition of the polymer chains, and in particular the ratio of the L- to the D-isomer of lactic acid, affect the processing, crystallization and degradation behaviour of PLA. By using copolymerization of L-lactide and meso-L,D- or racemic lactide, high molecular weight amorphous or semicrystalline polymers with a melting range from 130 to 185° C. can be obtained. Poly (L-lactide) (PLLA), a homopolymer comprising only L-lactide, is a semicrystalline and has the highest melting point, whereas PLA copolymers with higher D-isomer content exhibits lower melting points and dramatically lower crystallization behaviour, becoming amorphous at D-contents higher than 12-15%.

PLA is an aliphatic polyester and is, therefore, susceptible to hydrolytic degradation because of the ester groups present in its structure. The hydrolytic degradation behaviour, rate and mechanism are controllable by varying the molecular and higher order structures and by medium factors such as temperature, pH and the catalytic species (for example alkali and enzyme) of PLA. The in vivo hydrolytic degradation rate is comparable to in vitro degradation and, therefore, the in vivo degradation can be predicted to a certain extent from in vitro degradation behaviour and rate. PLA does not require the presence of enzymes to catalyse the hydrolysis. Lactic acid occurs in the metabolism of living organisms and, as a result, the degradation products of PLA are non-toxic.

The hydrolysis of aliphatic polyesters starts with a water uptake into the matrix that is followed by the hydrolytic splitting of the ester bonds. The initial degree of crystallinity affects the hydrolytic degradation rate as the amorphous parts have the higher rate of water uptake and the crystal segments reduce the water permeation in the matrix. Also, the autocatalytic effect of a PLA specimen has been reported. The autocatalysis is due to the increasing number of compounds containing carboxylic end groups in the centre of a specimen when low molar mass compounds cannot permeate the outer shell where the degradation products dissolve in the surrounding solution.

PLAs can be processed into various forms due to their thermoplastic nature. Melt processing is the most widely used method for PLA. In addition, injection moulding and extrusion are widely used methods to fabricate PLA films and fibers for different nonwovens or textiles. Also, the electro-spinning of PLA is used for medical applications to produce thin fibers that can be used as medical tissue scaffolds, wound dressings, carriers for drugs, protective fabrics and nanocomposite materials. The wide range of medical applications of PLAs includes orthopaedic screws, tissue engineering scaffolds, sutures, protein encapsulation and delivery, microspheres and drug delivery systems. PLLA is a slow-degrading polymer (between 2 to over 5 years for total resorption in vivo) with good tensile strength, low extension and high modulus. That is why PLLA is considered to be ideal for load bearing applications such as orthopaedic fixation devices. PDLLA, on the other hand, degrades faster and loses its strength within 1-2 months and, when hydrolysed, undergoes a loss in mass within 12-16 months. It also has lower tensile strength compared with PLLA. For that reason, PDLLA is preferred as drug delivery vehicles and as a low strength scaffold material for tissue engineering. PLLA (semi crystalline), PLDLA (amorphous), P(UDL)LA 70/30 (amorphous) and P(UD)LA 96/4 (semi crystalline) are the most commonly used PLA polymers in the medical industry.

Polylactide-Based Co-Polymers

PLGA is the most studied degradable polymer for biomedical applications. Because PLA and PGA have significantly different properties, different copolymer compositions allow PLGA to be optimized for different applications. With 25-75% lactide composition, PLGA forms amorphous polymers that are very hydrolytically unstable compared with the more stable homopolymers. A number of different processing techniques have been used for PLGA scaffold manufacturing, such as gas foaming, microsphere sintering, porogen leaching, electrospinning and polymer printing. Because of the rapid degradation of PLGA compared with other polyesters, PLGA has been especially used as sutures and drug delivery devices. PLGA has also been fabricated into tissue engineering scaffolds, since it demonstrates great cell adhesion and proliferation properties.

As mentioned above, in the present context the term PLA covers all polylactide polymers, (also called polylactic acid polymers) and copolymers with lactide and glycolide. In specific embodiments, PLA is a polylactide polymer.

Regarding stability, PLA contains ester bonds that may be degraded into lower molecular weight PLA's, or into monomers, dimers etc. In the present method, measures are taken to avoid extensive degradation. The degradation rate is dependent of temperature and pH. In a method of the present invention, after the melt spinning, at least some of the, or all, process steps are carried out at the most at room temperature, i.e. at the most at 25-30° C., such as at the most at 25° C. and a few of the process steps (e.g. some steps in drying and sterilization) are carried out at a temperature markedly lower than room temperature, such as at 0° C. or even lower, such as at no more than −10, −20 or −25° C.

The stability of the PLA component of the PLA-collagen scaffold may be ensured after processing by change in inherent viscosity or in the monomer amount (see e.g. Example 1 herein). The overall stability of the PLA-collagen scaffold may be ensured after all processing steps, for example by biomechanical characterization, as shown in Examples 2 and 3 herein.

Definitions

As used herein, "a three dimensional material" or "a three dimensional structure" refers to any material that has height, width and depth. One example of a three dimensional structure is a scaffold. The three dimensional material of the present invention is preferably implantable, biodegradable and biocompatible.

As defined herein, a "biodegradable material" is a material, which after introduction into the body requires no retrieval or further manipulation because it is degraded into soluble and non-toxic by-products.

As defined herein, a "implantable material" is a material of any shape or size, which is suitable for implanting to a subject.

As defined herein, a "biocompatible material" is a material that is not harmful or toxic to living tissue.

As defined herein, "loading" e.g. loading of collagen into a fiber mesh is intended to mean a process whereby collagen is added to the fiber or brought into contact with the fiber mesh so that collagen may be found on top of the fiber mesh, incorporated into the fiber mesh or both, or the fiber mesh is impregnated with collagen.

The term "biomechanical strength", as used herein, is intended to refer to the ability of a scaffold to be applied on biological tissues keeping its functionality, without breaking into pieces and to the ability of a scaffold to withstand normal handling of the scaffold after manufacturing, during storage and during application.

The term "mechanical strength", as used herein is intended to refer to the ability of a scaffold to withstand normal handling of the scaffold after manufacturing, during storage and during application. In this context, "mechanical strength" is sometimes used synonymously with "biomechanical strength" and with "biomechanical function".

In the present context, a desired improvement of biomechanical properties means i) an increase in one or more biomechanical parameters or biomechanical features, ii) a decrease in one or more biomechanical parameters or biomechanical features, or iii) no change in one or more biomechanical parameters or biomechanical features. The improvement is based on measurement of biomechanical features or biomechanical parameters of a scaffold prepared according to the invention compared with a scaffold prepared by the same method, but where the last step of sterilization is omitted. A desired improvement is when an increase (or decrease) is 1% or more, 2% or more, 3% or more, 4% or more, 5% or more, 6% or more, 7% or more, 8% or more, 9% or more or 10% or more; or when no change is less than 10%, less than 9%, less than 8%, less than 7%, less than 6%, less than 5%, less than 4%, less than 3%, less than 2% or less than 1%. The data used are mean values based on two or more measurements.

In the present context, relevant biomechanical features or biomechanical parameters include: Invariant modulus, invariant creep modulus (i.e. invariant modulus under creep conditions), dynamic invariant modulus, memory value, fluid mobility, apparent permeability, permeability in creep (i.e. apparent permeability under creep conditions), dynamic modulus (i.e. stress/strain ratio) and stiffness (i.e. the stress/strain ratio of a material). The parameters are further defined in the Experimental section herein.

In the present context, the term "creep test" is explained as follows: The nature of a creep test is pseudo-static (change of strain in time at constantly applied stress) and is often used to evaluate viscoelastic nature of materials and to approximate it with some models.

As used herein, the term "fibrous" refers to a material made of fibers. Fibers having diameters of only one size or different sizes may be used in the preparation of the mesh for use in a method of the present invention. These polymer fibers may be selected from PLA fibers having a diameter of from 5 to 100 μm, such as from 5 to 75 μm, from 5 to 50 μm, from 5 to 40 μm, from 5 to 35 μm, from 10 to 75 μm, from 10 to 50 μm, from 10 to 40 μm, from 10 to 35 μm, from 15 to 75 μm, from 15 to 50 μm, from 15 to 40 μm, or from 15 to 35 μm. The diameters are average diameters of the fibers in the structure. The cross-section of the fiber is not limited only to a round one but may also be any other shape, such as oval, starshaped, right-angled or a triangle.

In the present context, "porosity" is calculated as follows: Porosity=pore volume/specimen volume×100%. As well, the porosity is considered to be evaluated by micro-computed tomography (microCT) wherein the overall 3D structure of the structure can be analysed.

In the present context, a "bioactive" is a substance, compound and/or a living material that has biological activity or pharmacological activity, i.e. an effect on a living organism, tissue and/or cell, such as, but not limited to beneficial or adverse effects of a drug on living matter. When a drug is a complex chemical mixture, this activity is exerted by the substance's active ingredient or pharmacophore but can be modified by the other constituents. Typical examples are antibiotics, enzymes and vitamins, grafts and cells.

In the present context, the term "about" is intended to denote a range corresponding to a range from the stated value−10% to the stated value+10%.

Methods for Obtaining Fibers and Fiber Mesh

Fibers of the PLA polymer may be obtained by various methods well-known to a person skilled in the art. They may be obtained by melt processing or electrospinning. As it appears from the examples herein, melt spinning has proved to be suitable in the preparation of PLA fibers for use in a method of the present invention.

A melt spinning process involves melting of the polymer or heating the polymer to a soft form. Therefore, depending on the choice of specific polymer, a suitable temperature is selected for the spinning process. Typically, the temperature is in a range of from about 60 to about 300° C., such as in a range from about 70 to about 250° C., when polylactide is used.

Polylactides can be either amorphous or semicrystalline, depending on the ratio between L- and D-lactide monomers. Polyglycolide is semicrystalline. PLA is a brittle polymer with a melting point range of approximately 170-180° C. and a glass transition temperature of approximately 63° C. The glass transition temperature of P(L/D)LA is approximately 60° C. and the semicrystalline poly(L,D-lactides) have an approximate melting range of 135-170° C. Amorphous polymers do not have a melting point. Polyglycolide is produced by ring-opening polymerization of glycolide. It has approximately 45-55% crystallinity. It has a high melting point (−225° C.) and a glass transition temperature of −35° C. Polyglycolide degrades relatively quickly into acidic products.

In general, a melt spinning process of the PLA is performed at a temperature in a range of from about 60° C. to 300° C.

PLA raw material is dried before spinning and protective gas is used to prevent degradation during the spinning process.

The melt spinning process results in PLA fibers that are suitable for the PLA fiber mesh for use in the present invention. Some changes in the PLA material may take place during the spinning process, but these changes should not have major impact on the suitability of using the resulting fiber mesh to obtain the PLA-collagen scaffold. The resulting fibers are semicrystalline. In general, the resulting fibers have a monomer content close to the initial monomer amount of PLA and/or less than 30%, 25% or 20% decrease in inherent viscosity, compared to the raw material. This applies especially in cases, wherein the PLA raw material has an inherent viscosity of at the most 2.5 dl/g. However, if the PLA raw material has an inherent viscosity of from 2.5 to about 5 dl/g, the resulting fibers may have a decrease in inherent viscosity of about 70% or less, such as about 60% or less, about 50% or less, about 40% or less, about 30% or less, about 25% or less, or about 20% or less. In general, suitable scaffolds are obtained if the fibers resulting from the spinning process have an inherent viscosity in a range of from 1.5 to about 5 dl/g, such as from 1.5 to 4 dl/g, or from about 1.5 to about 3 dl/g. The inherent viscosity is determined as described herein at room temperature.

When the fibers have been obtained, they are transformed into a mesh. As described above, the mesh may be carded to form a 3D network. Carding is a mechanical process that disentangles and intermixes fibers to produce a continuous randomly oriented web, i.e. a carded mesh or a fibrous network. Carding breaks up locks and unorganized clumps of staples of fibers and then aligns the individual fibers to be mostly separated from each other. In order to obtain a desired porosity of the thus obtained network, the network may be subjected to needle punching, which is a process that uses needles with notches along the shaft of the needle that grabs the top layer of fibers and tangles them with the inner layer of fibers as the needle enters the fiber mesh/mat. Needle punching creates tangled and compressed 3D network from card and improves the mechanical properties, still leaving the structure highly porous.

The thus obtained fiber mesh, or fiber 3D network, has a porosity of at least 85%. Exemplary porosities are 85%, 86%, 87%, 88%, 89%, 90%, 91%, 92%, 93%, 94%, 95%, 96%, 97%, 98% and 99%. Accordingly, the 3D network may have a porosity of from 85 to 99%. As defined herein, the porosity, i.e., a void fraction is a measure of the void (i.e., "empty") spaces in a material, and is a fraction of the volume of voids over the total volume. The mesh or 3D network obtained has a porous structure, notably with pore network throughout the material.

The fiber mesh, or 3D network, may be cut into desired forms and/or sizes.

The thickness of the 3D network obtained is typically from 0.1 to 50 mm.

Loading Collagen to the Fiber Mesh

Prior to loading the fiber mesh or 3D network with collagen, the fiber mesh or 3D network may be subjected to a washing procedure. The washing procedure is typically carried out with an aqueous medium, in an alcohol-aqueous medium, or in an alcohol, such as ethanol. The washing procedure may be carried out several times and is followed by drying of the mesh or 3D network. The drying may be performed by freeze-drying or by drying at room temperature e.g. in a laminar hood. The fiber mesh or 3D network may also be cut into pieces of a size suitable for the intended use.

The fiber mesh or 3D network obtained are loaded with a collagen. The loading may be made to ensure a loading mainly on the outer surfaces of the mesh or 3D network, or it may be performed to load the collagen into the voids of the mesh or 3D network. The collagen may also adhere to the fibers of the mesh or 3D network. It is likely that collagen is present in the mesh or 3D network by a combination, e.g. the collagen may be present on the surface e.g. by adhesion, the collagen may be present in the voids e.g. by capillary forces and/or on the surfaces by adhesion. It is envisaged that the mechanisms by which collagen is contained in the scaffold are not of primary concern, but in the present context it is contemplated that the collagen is present in voids and surfaces of the mesh or 3D network.

Typically, the loading of collagen involves dissolving or dispersing collagen in a suitable medium. In general, the medium is an aqueous medium. pH and/or the viscosity of the aqueous medium containing collagen may be adjusted.

The concentration of collagen in the suitable medium is from about 0.1% to about 5% w/w such as from about 0.1% to 4% w/w, from 0.1% to about 3% w/w, from about 0.1% to about 2% w/w, The mesh or 3D network may then be immersed in the collagen-containing medium. Alternatively, the mesh or 3D network may be immersed in a solvent (which does not dissolve the scaffold), and a solution/dispersion of collagen is added to the immersed mesh or 3D network. Collagen may also be loaded into the mesh or 3D network by injection or spraying the collagen-containing medium into the mesh or 3D network.

The pH of the collagen aqueous medium should stay under 8 during processing. The process is preferably done at room temperature (RT) but may be done elevated temperatures, not exceeding 45° C. The weight ratio of PLA: collagen is from about 95 wt % to about 60 wt % of PLA and 40 wt % to about 5 wt % of collagen, and preferably from about 90 wt % to 75% of PLA and 25 wt % to 10 wt % of collagen. The weight ratio between PLA and collagen (PLA/collagen) is thus from 60/40 to 95/5 such as from 70/30 to 90/10, from 75/25 to 80/20, or from 80/20 to 90/10. The porosity of PLA-collagen scaffold prior to a possible loading with cells, drugs, etc. is from about 70% to 99%, and preferably from about 80% to 95%, As defined herein, recombinant human collagen refers to a human collagen polypeptide, which is produced by using recombinant techniques, e.g. using appropriate polynucleotides, expression vectors and host cells. Recombinant techniques are well known to a person skilled in the art and for example several commercial recombinant human collagens are present on the market. Use of recombinant human collagen lowers the risks of transmitting known and unknown animal-derived pathogens and undesirable immunological responses. In addition, unlike other naturally derived materials for cartilage regeneration, the recombinant human collagen does not suffer from batch-to-batch variability. Accordingly, recombinant human collagens can be produced in a grade required by good manufacturing practices (GMP), in high amounts and of uniform quality.

Collagen is the most abundant protein in the extracellular matrix (ECM) and is the major component of skin and musculoskeletal tissues. At least 28 different types of collagen have been identified to date. All collagens have a triple-helical structure where three individual chains, each in a left-handed polyproline II-helix, are coiled together to form a right-handed, super coiled triple helix with a rope-like structure. In this structure, collagens show a characteristic repeating sequence, glycine-X-Y, where glycine is a small enough amino acid to pack into the centre of the triple-helical structure. X and Y positions can be any amino acid, but X is often proline and Y is frequently hydroxyproline. Collagens can be divided into different groups based on their structure and supramolecular organization. These groups are fibril-forming collagens, fibril-associated collagens (FACIT), network-forming collagens, anchoring fibrils, transmembrane collagens, basement membrane collagens and others, each with a unique function. The most abundant group of collagens are the fibril-forming collagens with about 90% of the total collagen. Collagen type I is the most abundant and the best studied collagen and forms more than 90% of the organic mass of bone and is the major collagen in tendons, skin, ligaments, cornea and many interstitial connective tissues, with the exception of only a few tissues such as hyaline cartilage, brain and vitreous body. Type II collagen, on the other hand, is the characteristic and predominant component of hyaline cartilage, but it is also found in the vitreous body, the corneal epithelium, notochord, the nucleus pulposus of intervertebral discs and embryonic epithelial-mesenchymal transitions.

Collagen possesses high mechanical strength, good biocompatibility, low antigenicity and the ability to cross-link, which enables the tailoring of the mechanical, degradation and water uptake properties of collagen. When fabricated into highly porous scaffolds, the cross-linking of collagen is necessary to fabricate scaffolds with adequate mechanical properties and degradation rate. Collagen has been extensively studied for use in various medical applications and a wide range of tissue engineering applications such as bone, cartilage and skin tissue engineering. Modifying or combining collagen with other degradable polymers improves the potential of collagen as a biomaterial. The principal collagen that can be readily prepared in a pure form in commercial quantities is type I collagen. It is the most widely used collagen for tissue engineering applications. Collagen scaffolds offer an alternative way to provide biological information to the growing construct, unlike biodegradable synthetic polymers. While using collagen scaffolds, a wide range of cell adhesion and other signals that will enhance the quality of the tissue-engineered products is achieved. Generally, freeze-drying or stereolithography methods are used for fabricating porous, collagen-based scaffolds and carbodiimide is often applied for cross-linking. Porous collagen scaffolds are often combined with other components such as, bioceramics or synthetic biodegradable polymers. Collagen is already available in a variety of commercial medical products, such as a bioprosthetic heart valve or as a wound dressing. The use of collagens can be divided into two different categories: tissue-based devices where natural, stabilised tissue is used as a device (a bioprosthetic heart valve) and purified collagen, where collagen is made soluble through an enzyme digestion step and reconstituted into various products (a wound dressing).

Recombinant collagens are emerging since they offer a way to produce high purity and non-disease carrying collagens with the possibility to produce all types of collagens, even those with very low abundance in natural tissue.

Suitable collagens for use in a method of the present invention are collagens from any source including animal derived, human, recombinant or synthetic collagen. The collagen may be collagen type I, II, III, IV, V, VI, IX or XI. Any combination of these collagen types may also be utilized. The collagen is more specifically collagen type I, II or III. The collagen may also be a combination of at least type I, II and III collagens, at least type I and III collagens, at least type I and II collagens, or at least type II and III collagens. Any collagen may also be used in combination with an animal derived, recombinant or synthetic collagen, or the collagen may be used alone or in combination with other collagens.

As used herein "the recombinant human collagen material" refers to any material (e.g. any solution or gel) comprising recombinant human collagen.

The collagen for use in a method of the present invention may be porous. For example, freeze-drying makes the collagen porous and elastic and thus well suitable for its purpose, e.g. to support chondrocyte proliferation and cartilage matrix production. Collagen, such as freeze-dried collagen network, is an excellent microenvironment for cell attachment. In embodiments of the invention the collagen is freeze-dried. The collagen (e.g. in the form of collagen solution) may be freeze-dried as such. Pore size of the collagen structure varies between 20-250 μm, and can be selected from 20-250 μm, 50-250 μm, 30-200 μm, 40-200 μm, 50-200 μm, or 60-200 μm. Also, it is possible to convert the collagen into a gel before freeze-drying, i.e. the collagen(s) may be in the form of a freeze-dried gel.

Collagen is used in scaffolds, which may be used in tissue repair and regeneration, whether in sponges, sheets, or gels. It is believed that collagen scaffolds have the correct properties for enabling tissue regeneration such as pore structure, permeability, and hydrophilicity. Collagen scaffolds support cell adhesion, robust cell spreading, proliferation and differentiation in 3D.

The thus obtained PLA-collagen scaffold may then be dried. The drying may involve freeze-drying optionally with a preceding step of freezing the wet scaffold for over 10 h at −20 to −50° C. The freezing is depended on the used materials as well as size of the specimen, taking generally over 10 hours. The freezing temperature effects the size of the forming pores in the structure and is also depended on the used materials. The freezing temperature is generally varying from −10° C. to −80° C. and is preferable between −20° C. to −50° C. The freeze-drying process is usually done in same temperature ranges or lower temperatures as the freezing process. The freeze-drying time is depended on used materials as well as size of the specimen and varies usually from 24 hours to 48 hours.

After loading the mesh or 3D network with one or more collagens and optionally drying a PLA-collagen scaffold is obtained, which is preferably subjected to cross-linking of the collagen in the PLA-collagen scaffold. Cross-linking is made to increase the biomechanical strength of the final scaffold and to make the collagen component more stable in vivo.

Suitable cross-linking methods are well known to a person skilled in the art and include but are not limited to the use of chemical cross-linking agents such as to 1-ethyl-3-(3-dimethylaminopropyl)-carbodiimide (EDC), glutaraldehyde, genipin, and also UV light, or a combination thereof.

A suitable combination of cross-linking agents is EDC and preferably EDC is used together with N-hydroxysuccinimide (NHS). The cross-linking is typically performed in an alcoholic medium such as in ethanol-water solvents. The content of ethanol is usually from 50 wt % to 99 wt % such as from 60 wt % to 99 wt %, from 70 wt % to 99 wt %, from 80 wt % to 99 wt % or from 90 wt % to 99 wt %.

Cross-linking is typically performed by use of EDC and NHS. The concentration of EDC may be in a range of from 5 to 30 mM such as from 5 to 25 mM, from 10 to 20 mM, such as 14 mM EDC. The concentration of NHS may be in a range of from 1 to 15 mM such as from 1 to 10 mM, from 5 to 10 mm or about 6 mM NHS.

The cross-linked PLA-collagen scaffold is extensively washed typically with an aqueous medium including water, an alcoholic aqueous medium or an alcohol to avoid cross-linking residues.

Then the cross-linked PLA-collagen scaffold is dried. The drying may involve freeze-drying, optionally with a preceding step of freezing the wet scaffold for over 10 h at −20 to −50° C. Details regarding freeze-drying and freezing are the same as those mentioned hereinbefore. The temperature may have an impact on the size of the pores in the final product; thus, the lower the temperature, the smaller size of pores.

Sterilization of the Dry PLA-Collagen Scaffold

The scaffold, on top of being otherwise safe to use and function properly in e.g. an AC environment, should also be sterile prior to implantation. One of the most reliable sterilization methods for implantable medical devices is gamma irradiation. Gamma irradiation is highly effective and there are no residual chemicals that can cause cytotoxicity. However, gamma irradiation is known to influence on the properties of biodegradable polymers, such as PLAs, as well on collagens. Especially collagens may suffer from loss of mechanical integrity while too high level of irradiation. Collagens are temperature sensitive and high temperature rise should be avoided during processing as well as sterilization.

After drying of the PLA-collagen scaffold it is sterilized resulting in the sterile PLA-collagen scaffold. Any suitable method can be used which does not lead to unwanted degradation of the PLA, the collagen or the PLA-collagen scaffold. A suitable method is to subject the PLA-collagen scaffold to gamma irradiation, but as mentioned herein before any temperature rise should be avoided to avoid any deterioration of the collagen component. Irradiation is a process involving transfer of energy and therefore, the process should be carried out under temperature-controlled conditions for sensitive materials, such as collagen. A method for keeping the temperature low is to cool the PLA-collagen scaffold during the irradiation process. The scaffold is typically cooled to a temperature of from about −200° C. to about 25° C. before sterilizing is performed. By this method the temperature during sterilization stays under 40 degrees.

The temperature of the PLA-collagen scaffold before sterilizing is essentially the same or higher than the temperature of the PLA-collagen scaffold during sterilizing.

The sterilization is typically carried out at a temperature in a range of from −200° C. to 40° C. such as at the most 30° C. or at the most at 25° C., or in a temperature in a range from −100° C. 25° C. such as at a temperature of −70° C., −40° C., 0° C., 10° C., 20° C. or 25° C.

As it appears from the examples herein, the dose used—when sterilization is made by gamma irradiation—is typically in a range of from 10 kGy to about 27 kGy such as from 15 to 26 kGy, from 16 to 25 kGy such as 18 kGy, 19 kGy, 20 kGy, 21 kGy, 22 kGy, 23 kGy, 24 kGy, 25 kGy, 26 kGy or 27 kGy.

Normally, the PLA-collagen scaffold is packed in suitable packages before sterilization to ensure the remaining of the sterility of the scaffold after the sterilization process.

It should be mentioned that sterilization may also occur in optional steps of the method of the invention. Thus, the fiber mesh (PLA mesh) may be subject to sterilization before loaded with collagen and the collagen itself may be sterilized before loading into the PLA fiber mesh or 3D network.

A major advantage of employment of the sterilization process is that the resulting sterile scaffold has very uniform biomechanical properties. As seen in example 3, a scaffold, that has been not subjected to sterilization, but has been manufactured aseptically, has much more varying biomechanical properties. From a regulatory point of view, it is a major advantage to be able to prepare scaffolds without marked batch to batch variation in the properties. The reason being that the biomechanical properties give an indication of how the scaffold will behave in vivo and it is desired that the in vivo behavior can be foreseen, i.e. no or only little variation has minor impact on the in vivo properties, whereas greater variation may have impact on in vivo properties and it will be needed to investigate whether such an impact negatively influences the effect of the scaffold (e.g. stability of the scaffold, ability to stay on the administration site, negative influence regarding release of cells or bioactive agents, undesired side-effects etc). Therefore, strict control of obtaining identical or almost identical biomechanical properties is desired—also in connection with regulatory approval. In general variation in properties of ±10% is normally acceptable.

As seen from the Examples herein scaffold prepared according to the invention has improved biomechanical properties compared with an unsterilized scaffold.

The improved biomechanical properties can be expressed as a change in one or more biomechanical parameters or biomechanical features such as invariant modulus, invariant creep modulus (i.e. invariant modulus under creep conditions), dynamic invariant modulus, memory value, fluid mobility, apparent permeability, permeability in creep (i.e. apparent permeability under creep conditions), dynamic modulus (i.e. stress/strain ratio) and stiffness (i.e. the stress/strain ratio of a material). The desired change may be i) an increase, ii) a decrease, or iii) no change.

In an aspect, the one or more biomechanical parameters or biomechanical features is/are selected from invariant creep modulus, when tested under wet conditions, and dynamic modulus, when tested under dry conditions. A desired change compared with a non-sterilized scaffold is an increase. Typically, an increase is 1% or more, 2% or more, 3% or more, 4% or more, 5% or more, 6% or more, 7% or more, 8% or more, 9% or more or 10% or more.

Some biomechanical parameters may decrease or do not change. Such parameters include biomechanical parameters or biomechanical features selected from permeability in creep and dynamic modulus, both determined under wet conditions. A desired decrease is 1% or more, 2% or more, 3% or more, 4% or more, 5% or more, 6% or more, 7% or more, 8% or more, 9% or more or 10% or more, whereas no change is less than 10%, less than 9%, less than 8%, less than 7%, less than 6%, less than 5%, less than 4%, less than 3%, less than 2% or less than 1%.

In particular, the improved biomechanical properties are improved stiffness.

All details regarding the individual steps as mentioned in the main aspect of the invention apply mutatis mutandis for all other aspects of the invention and are therefore not in the following paragraphs.

Other Aspects of the Invention

The present invention also relates to a method for preparing a sterilized PLA-collagen scaffold, the method comprising a) providing PLA in solid form
b) subjecting PLA to a process whereby fibers of PLA are obtained, and
c) subjecting the obtained fibers to a process, whereby a mesh of fibers is obtained,
d) optionally subjecting the mesh of fibers to carding and/or needle punching to obtain a 3D network of PLA fibers,
e) optionally, subjecting the mesh of fibers or the 3D network of fibers to one or more washing procedures,
f) providing a collagen in the form of a solution or a gel,
g) immersing in the collagen solution or collagen gel the mesh of fibers or the 3D network of fibers obtained after step c) or, if included after step d) or e) to obtain a PLA-collagen scaffold,
h) optionally, drying the PLA-collagen scaffold, and
i) sterilizing the PLA-collagen scaffold obtained in step g) or, if included, in step h).

The present invention also relates to a method for preparing a sterilized PLA-collagen scaffold, the method comprising a) providing PLA in solid form,
b) subjecting PLA to a process whereby fibers of PLA are obtained,
c) subjecting the obtained fibers to a process, whereby a mesh of fibers is obtained,
d) subjecting the mesh of fibers to carding and/or needle punching to obtain a 3D network of PLA fibers,
e) optionally, subjecting the mesh of fibers or the 3D network of fibers to one or more washing procedures,
f) providing a collagen in the form of a solution or a gel,
g) immersing in the collagen solution or the collagen gel the mesh of fibers or the 3D network of fibers obtained after step d) or, if included after step e) to obtain a PLA-collagen scaffold,
h) optionally, drying the PLA-collagen scaffold, and
i) sterilizing the PLA-collagen scaffold obtained in step g) or, if included, in step h).

The present invention also relates to a method for preparing a sterilized PLA-collagen scaffold, the method comprising a) providing PLA in solid form,
b) subjecting PLA to a process whereby fibers of PLA are obtained,
c) subjecting the obtained fibers to a process, whereby a mesh of fibers is obtained,
d) subjecting the mesh of fibers to carding and/or needle punching to obtain a 3D network of PLA fibers,
e) subjecting the 3D network of fibers to one or more washing procedures,
f) providing a collagen in the form of a solution or a gel,
g) immersing in the collagen solution or collagen gel the 3D network of fibers obtained after step e) to obtain a PLA-collagen scaffold,
h) optionally, drying the PLA-collagen scaffold, and
i) sterilizing the PLA-collagen scaffold obtained in step g) or, if included, in step h).

The present invention also relates to a method for preparing a sterilized PLA-collagen scaffold, the method comprising a) providing PLA in solid form,
b) subjecting PLA to a process whereby fibers of PLA are obtained,
c) subjecting the obtained fibers to a process, whereby a mesh of fibers is obtained,
d) subjecting the mesh of fibers to carding and/or needle punching to obtain a 3D network of PLA fibers,
e) subjecting the 3D network of fibers to one or more washing procedures,
f) providing a collagen in the form of a solution or a gel,
g) immersing in the collagen solution or the collagen gel the 3D network of fibers obtained after step e) to obtain a PLA-collagen scaffold,
h) drying the PLA-collagen scaffold, and
i) sterilizing the PLA-collagen scaffold obtained in step h).

Use of a scaffold prepared by a method of the invention

A scaffold obtained according to the invention is typically used in human and veterinary surgical care. It may also be used in other health and medical care in humans and animals, namely companion animals, and in cosmetics.

A scaffold obtained according to the present invention may be used in the treatment of lesions of articulating joint surfaces, especially in weight-bearing joints, such as the knee. These lesions manifest symptoms, such as pain and locking of the affected joint, and require surgical intervention. These lesions vary in etiology, but the cartilage injury can be the result of trauma, degenerative joint disease, such as osteoarthritis (OA), and developmental disorder, such as osteochondritis dissecans.

The scaffold may be used as such or it may be loaded or combined with one or more of: tissue-specific cells, such as chondrocytes, somatic or embryonic stem cells, such as mesenchymal stromal cells from bone marrow, cellular components, such as growth-factors or cytokines, blood-components and fractions, such as platelets or platelet-rich plasma, or drug substances, such as an anti-inflammatory drug, such as ibuprofen. Paramount for the above-mentioned conditions is using a scaffold of present invention as a lesion filler and, as a secondary importance, incorporating the potential additives.

A scaffold obtained according to the invention may also be used in cosmetic surgery, e.g. as a dermal filler in facial enhancement.

A scaffold is typically surgically delivered, i.e. implanted into the body. It can be used in chondral or osteochondral lesions. In connection with cartilage-related condition, a scaffold is implanted to a debrided lesion site. The scaffold may be secured to the lesion bed by resorbable sutures or fibrin glue.

Figure 1A:
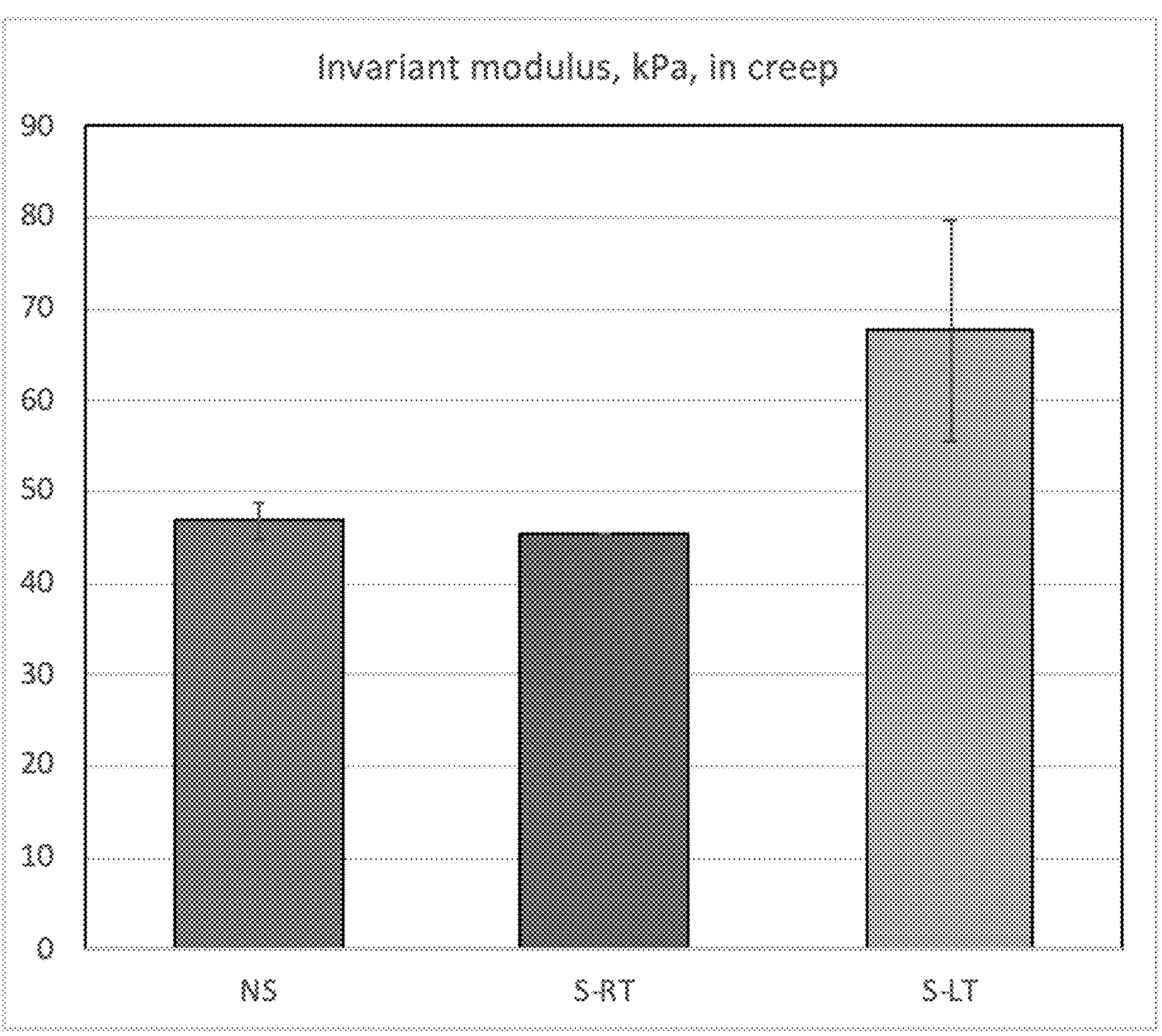
FIG. 1A. Obtained invariant modulus in creep tests, in wet conditions (see Example 3).

The invention is further illustrated in the following, non-limiting examples.

EXAMPLES

Example 1

A method for preparing a sterilized scaffold for medical use with polylactide fibers and collagen, drying the structure by freeze-drying to achieve a scaffold and sterilizing the scaffolds to obtain sterilized and stabilized PLA-collagen scaffold, rhCo-PLA. In this example, it is demonstrated that the PLA component is not negatively affected by the processing method.

The scaffolds were manufactured as follows. A PLA component, medical grade poly(UD)lactide 96/4 (Corbion, Purac Biochem by, Gorinchem, The Netherlands) with an inherent viscosity in a range of from 1.8 dl/g to 2.2 dl/g and residual monomer amount less than 0.1% was used to manufacture thin fibers by melt spinning. Before melt spinning, the PLA raw material was dried in vacuum oven. The melt processing of the fibers was done with melt spinning under protective atmosphere within a temperature range of 70-240° C. The spinning equipment consists of micro-extruder and a high-speed spinning machine. The fibers were cut into staple fibers and carded into mesh. The PLA felt was manufactured by needle punching the carded PLA mesh. The PLA felt was washed and dried in a laminar hood and subsequently packed before placing into a clean room environment. Recombinant human type III collagen (FibroGen Ltd., CA, USA) fibril formation was done by increasing the pH of the collagen solution with basic buffer solution to 7. After formation of a collagen gel, the PLA felt was fully immersed with the collagen gel and placed into sample molds. These structures were then freeze-dried to achieve fully dried structures, i.e. rhCo-PLA scaffolds. The manufactured scaffolds were cross-linked with 95% ethanol solution with 14 mM EDC (N-[3-dimethylaminopropyl]-N'-ethylcarbodiimide hydrochloride, Sigma-Aldrich, Helsinki, Finland) and 6 mM NHS (N-Hydroxysuccinimide, Sigma-Aldrich, Helsinki, Finland) at room temperature (RT). The manufactured rhCo-PLA scaffolds were then washed, freeze-dried, and packed before sending to sterilization by gamma irradiation 25 kGy and under dry ice to avoid temperature rise during sterilization.

For the manufactured rhCo-PLA, the following studies were performed. The monomer amount measurement of L-lactide was done by GC-MS technique with lower limit of 0.01 wt % (Rambol Analytics, Lahti, Finland), the inherent viscosity (i.v.) was measured with a Lauda PVS viscometer (Lauda DR. R. Wobster GmbH, KG, Konigshofen, Germany). Samples were prepared by dissolving the polymer in 1 mg/ml chloroform. An Ubbelohde capillary viscometer type Oc (Schott-Geräte, Mainz, Germany) was used to determine the viscosity.

By this manufacturing method, a sterilized scaffold for medical use with polylactide fibers and collagen, rhCo-PLA, was achieved with following features, as seen in Table 1:

The residual monomer amount of the PLA component did not remarkably change, as the monomer amount stayed under 0.1 wt %, which was the same as the raw material monomer amount. The used PLA processing temperatures and sterilization did not extensively alter the inherent viscosity of the extruded PLA: acceptable decrease in this experiment was around 50%.

TABLE 1

| | Feature of PLA raw material | Feature of PLA component of the sterilized rhCo-PLA scaffold |
|---|---|---|
| Residual monomer amount in PLA component | <0.1 wt % | <0.1 wt % |
| Inherent viscosity of PLA component | 1.9 dl/g | 1.0 dl/g |

Example 2

A sterilized scaffold for medical use with polylactide fibers and collagen, manufactured by drying the structure by freeze-drying to achieve a scaffold and sterilizing the scaffolds to obtain sterilized PLA-collagen scaffold. A rhCo-PLA scaffold as described in Example 1 was sterilized with gamma irradiation and the effect of sterilization, especially to the collagen component, was evaluated. As well, different gamma irradiation doses (under dry ice), to show the effect of sterilization doses, were used on the rhCo-PLA scaffolds.

The data analysis was made according to the procedure described in detail in the U.S. patent Ser. No. 10/379,106 B2. This analysis comprises extraction of the invariant data such as viscous stiffness and memory values in static and dynamic conditions respectively from the data of applied load (stress) and deformation (strain). In this specification, the following definitions are used:

"Invariant modulus" is an intrinsic elastic modulus value which does not depend on time or frequency, and which can be used in the prediction of the material behavior (i.e. true value).

"Dynamic invariant modulus" is a ratio of dynamic stress amplitude to dynamic true (logarithmic) strain amplitude, expressed with real (not complex) algebra (different from commonly used real (storage) and imaginary (loss) moduli definition)

"Memory value" is a time-invariant property of the specimen, having the value in the range between zero and one, representing the viscous tendency of the material, even if the material itself is not a fluid. Memory values do not have a theoretical prediction and always must be determined from the experiment. In the present invention memory values have been experimentally measured separately for static (creep) and dynamic conditions as they were found to be different.

"Fluid mobility" is a measure (coefficient) of the rate of the fluid movement inside a porous body, analogues to the diffusion coefficient (using the same units in $mm^2/s$). Its nature however differs from the latter because as the movement of fluid is not only by diffusion but also due to convective part and momentum transfer. Fluid mobility describes how well fluid has a potential to flow inside under certain conditions.

"Apparent permeability" describes a capacity of a porous body to allow a fluid to pass through its porous network and it is measured in squared distance units ($m^2$). It is a quantified topological capacity of a material for transportation of a fluid through its porous structure and only depends on material structure but not on fluid properties. Here it differs from commonly defined permeability by Darcy law, as the latter requires an increase of the fluid pressure gradient across the material specimen. However, as shown in U.S. Pat. No. 10,379,106 B2, the method applied also here allows measurement of permeability without a knowledge of the fluid pressure gradient, and to distinguish between these methods, "apparent permeability" term is used (expressed in millidarcy; 1 mDarcy=$10^{-15}$ $m^2$).

A first test was done for aseptically produced rhCo-PLA (rhCo-PLA-A), which was compared to a rhCo-PLA sterilized with a standard irradiation dose, where the irradiation dose was 25 kGy. In the process, the actual irradiation dose was measured to be 29 kGy (rhCo-PLA-S). The aseptically produced rhCo-PLA (rhCo-PLA-A) had a gamma irradiated PLA component (sterilized with the standard irradiation dose 25 kGy), but the addition of the collagen component was done after sterilization, in aseptic conditions, i.e. the collagen component itself was not irradiated. Therefore, the PLA fiber component should have had identical properties and contribution to overall biomechanical performance, and the differences are mainly due to effect of collagen and its treatment.

The manufactured scaffolds were subsequently tested with a biomechanical testing procedure using dynamic mechanical analysis (DMA) in a standard compression sample holder (15 mm diameter) in the dynamic mechanical analyzer DMA242E (Netzsch Gerätebau GmbH, Selb, Germany).

A part of the scaffolds was subjected to a creep test under constant force of 0.2N stress and another part to oscillating forces causing strains in the range of 5-50 μm at 1 Hz frequency (strain-sweep method). Briefly, after letting the probe to establish the contact with the specimen and taring the offset, the starting height of the specimen immersed in media was again measured and used further as the starting height for true strain calculations.

In all cases, scaffolds were tested fully immersed in water at room temperature and allowing them to equilibrate 15 min before the measurements. All specimens thus have been fully impregnated, and no air bubbles or dry areas were observed. The cross-sectional area of the tested scaffolds was 20-26 $mm^2$. All tests were done up to 300 min (until dimensional changes were approaching constant values; displacement resolution±0.0005 μm). These data were stored and exported as ASCII text file into data processing software (Microsoft Excel complemented with customized code). The primary data were converted into stress and true strain, and the ratio of strain to stress vs. experiment time. After that, numerical algorithm of time convolution was applied and processed data were non-locally integrated pair-wisely, row by row with a mathematical method described in detail in U.S. Pat. No. 10,379,106 B2.

These experimental data are shown in Table 2.

TABLE 2

| | rhCo-PLA-A | rhCo-PLA-S |
|---|---|---|
| Irradiation dose on PLA, kGy | ≥25 | 29 |
| Irradiation dose on collagen, kGy | 0 | 29 |
| Creep test under 0.2N at 25° C. in water | | |
| Invariant modulus, kPa | 71.5 | 55.9 |
| Memory value | 0.089 | 0.051 |
| Fluid mobility, mm2/s | 0.129 | 0.072 |
| Apparent permeability, milliDarcy | 0.504 | 0.359 |
| Strain sweep at 1 Hz at 25° C. in water | | |
| Dynamic invariant modulus, kPa | 41.4 | 61.6 |

Table 2 indicates that the sterilization with the standard procedure of gamma irradiation with a dose 25 kGy affected the biomechanical properties of the rhCo-PLA scaffolds as follows:

In the creep test, with a sterilization dose of 29 kGy the rhCo-PLA-S scaffolds have suffered from decrease of invariant modulus which drop after irradiation significantly (−22%). The memory value has also decreased (−43%), indicating the rhCo-PLA scaffolds to become more elastic after the sterilization. The decrease of effective fluid mobility and apparent permeability of sterilized rhCo-PLA scaffolds (almost twice) indicates the state of less movable fluid inside the scaffold, and thus the irradiated scaffold structure becomes less permeable to fluid. These changes are undesirable, and such inferior biomechanical properties of rhCo-PLA-S are not acceptable. For the creep tests, this sterilization method was therefore found to major affect biomechanical characteristics of the rhCo-PLA scaffold, making it impossible to ensure its use for the intended application.

In the strain sweep test, the dynamic invariant modulus increased (+33%), indicating the rhCo-PLA-S scaffolds to become more rigid after the sterilization, which leads to their inferior ability to conform to dynamic strains in the surrounding tissue.

The second step was to evaluate more precise gamma irradiation dose effect on the rhCo-PLA scaffold. A study was done to compare the different, under the standard 25 kGy, doses of gamma irradiation to the rhCo-PLA scaffolds. Therefore, the sterilization with low dose of gamma irradiation for rhCo-PLA scaffolds was conducted with the following doses: 18 kGy (G18), 20 kGy (G20), 22 kGy, (G22), and 25 kGy (G25). The non-sterile rhCo-PLA scaffold (GO) was used as a reference.

The manufactured scaffolds were tested with biomechanical testing procedure using dynamic mechanical analysis, as described above, using the same dynamic mechanical analyzer DMA242E (Netzsch Gerätebau GmbH, Selb, Germany). The scaffolds were subjected to creep test under 0.2N constant force, similarly to the above. In all cases, scaffolds were tested fully immersed in water at room temperature and allowing them to equilibrate 15 min before the measurements. The area of the tested scaffolds was 37-46 mm$^2$.

The biomechanical test results for rhCo-PLA scaffolds with these different lower doses of gamma irradiations are shown in Table 3. The results indicate that these different amounts of gamma irradiation, 25 kGy gave no significant changes to the biomechanics of the rhCo-PLA scaffolds (this is seen as e.g. value of invariant modulus and memory values of GO samples are within the limits measured on sterilized samples G18-G25).

TABLE 3

| | G0 | G18 | G20 | G22 | G25 |
|---|---|---|---|---|---|
| Creep test under 0.2N at 25° C. in water | | | | | |
| Invariant modulus, kPa | 22.1 | 21.0 | 20.9 | 27.1 | 25.1 |
| Memory value | 0.041 | 0.041 | 0.052 | 0.037 | 0.039 |
| Fluid mobility, mm$^2$/s | 0.028 | 0.030 | 0.034 | 0.033 | 0.037 |
| Apparent permeability, mDarcy | 1.110 | 1.275 | 1.512 | 1.069 | 1.281 |

Example 3

A sterilized scaffold for medical use with polylactide fibers and collagen, manufactured by drying the structure by freeze-drying to achieve a scaffold and sterilizing the scaffolds to obtain sterilized PLA-collagen scaffold.

A rhCo-PLA scaffold as described in Example 1 was sterilized with gamma irradiation at RT (S-RT) or at lower temperature (−70° C.) (S-LT) and the effect of sterilization, was evaluated and compared to non-sterile scaffolds (NS). In this test the possible changes in biomechanical properties of the scaffolds were demonstrated by different sterilization methods under the same expected dose (25 kGy) in general and find out if the lowered temperature during sterilization has an effect on biomechanical properties. The biomechanical testing was done for dry samples as well as for wet samples as described below.

Biomechanical analysis was made in dry conditions till 60° C. and in wet immersed conditions at 25° C. in compression mode. The manufactured scaffolds were tested with a biomechanical testing procedure using dynamic mechanical analysis in a standard compression sample holder (15 mm diameter) in the dynamic mechanical analyzer DMA242E (Netzsch Gerätebau GmbH, Selb, Germany). A part of the scaffolds was subjected to a creep test under 0.2N constant force and another part to strain sweep in the amplitude range from 5 to 25 μm at 1 Hz frequency. For the latter the loading cycles were repeated 10 times, similarly to Example 2.

Scaffolds were tested as fully immersed in water at 25° C. allowing them to equilibrate 15 min before the measurements. All specimens thus have been fully impregnated, and no air bubbles or dry areas were observed. A set of dry specimens was additionally tested in dry conditions (air) under 1 Hz and 25 μm amplitude but upon heating to 60° C. with 2 K/min rate with the purpose to assess thermal stability of the mechanical properties.

The cross-sectional area of the tested scaffolds was 30-40 mm$^2$. The data analysis was made according to the procedure described in U.S. patent Ser. No. 10/379,106 B2, aimed on the extraction of the invariant data such as viscous stiffness and memory values in static and dynamic conditions respectively, with the data shown in FIG. 1-3. It is noteworthy to mention that under repetitive dynamic loading all specimens are progressively contracting with every loading sequence cycle. Hence the integral (slope) value of the dynamic stress/strain ratio ("standard dynamic modulus") and the associated static stress/strain ratio ("standard static modulus") at 1 Hz have been extracted to represent the values covering all loading cycles.

Figure 1B:
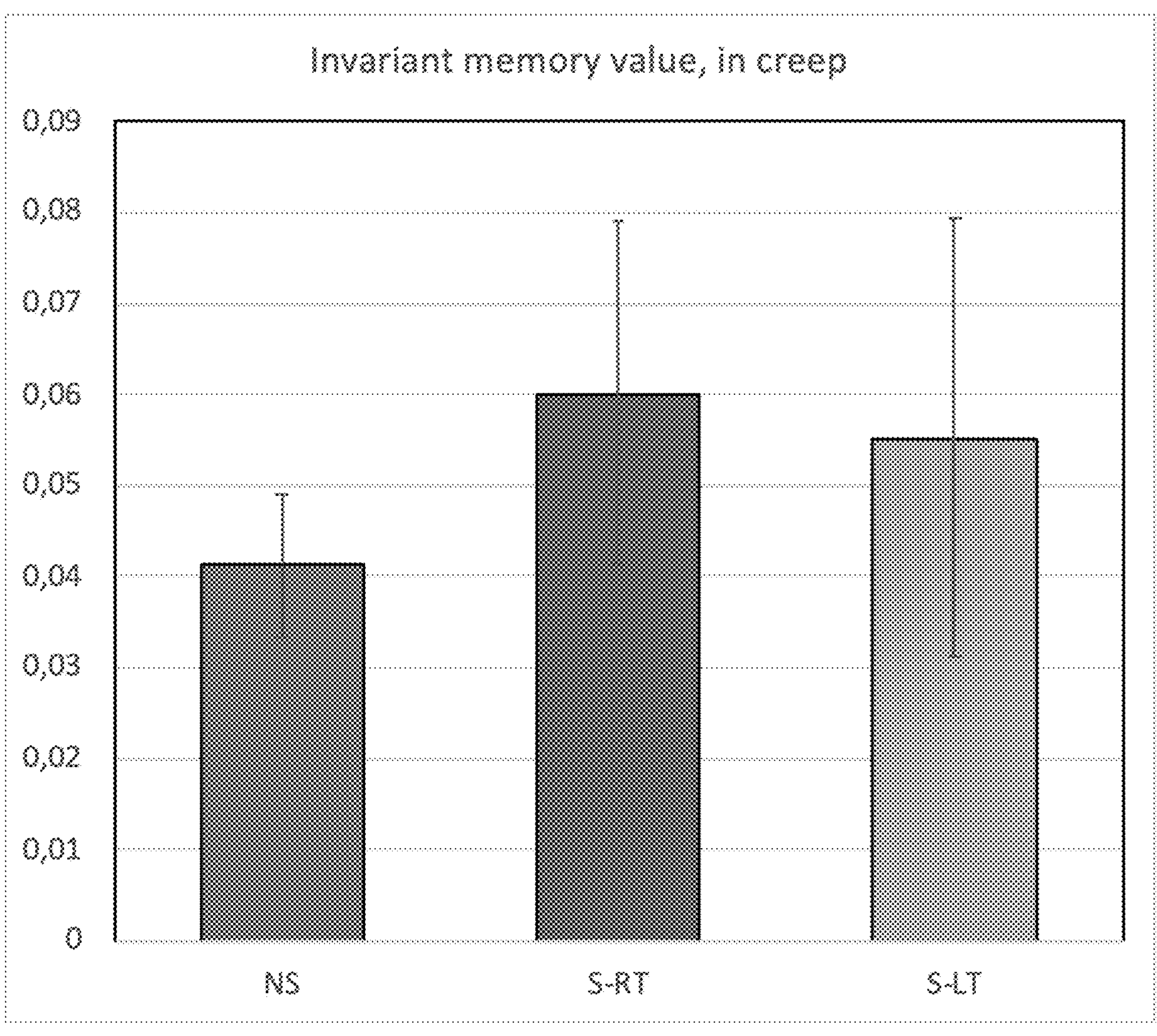
FIG. 1B. Obtained memory value in creep tests, in wet conditions (see Example 3).
Figure 1C:
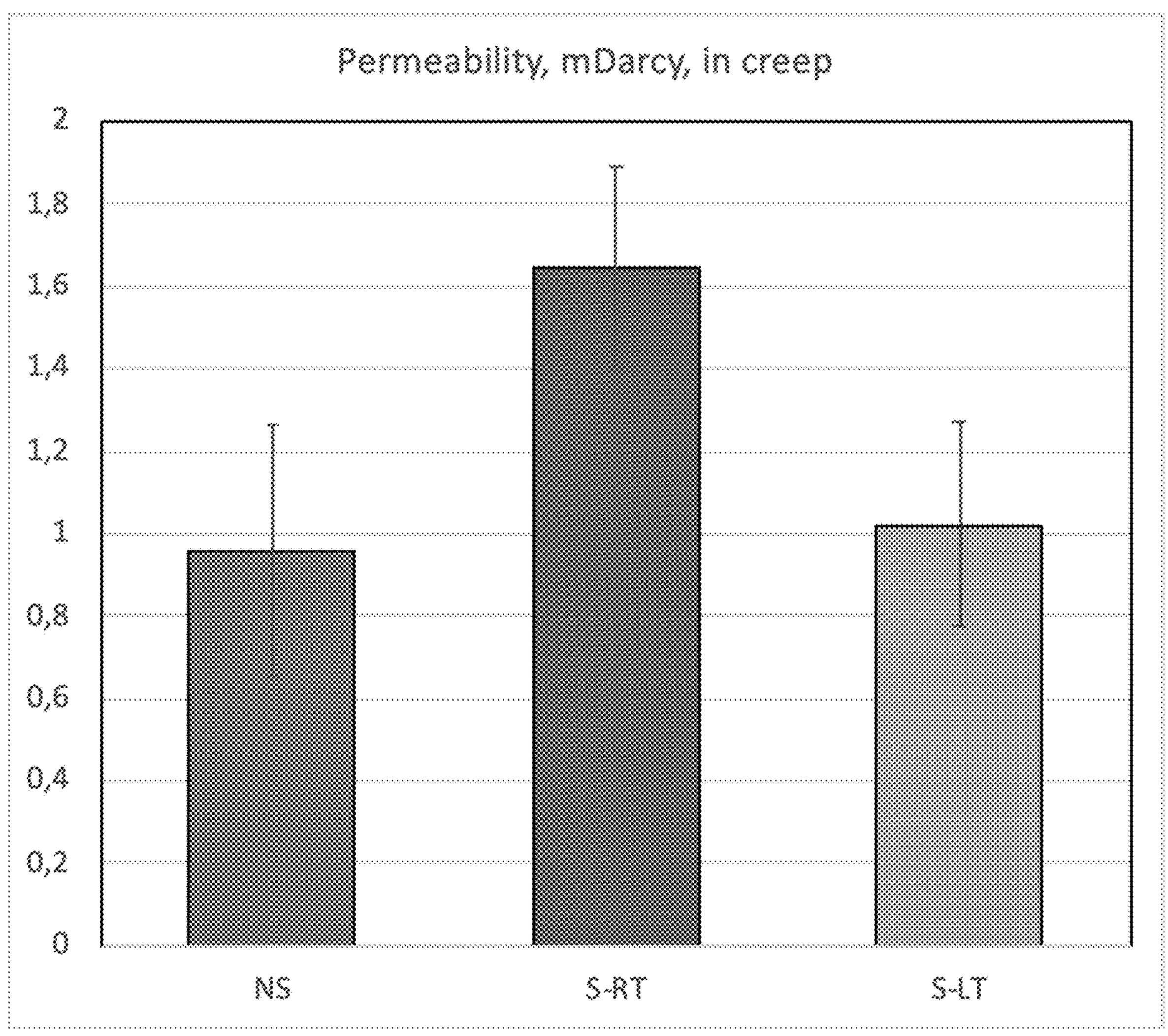
FIG. 1C. Obtained permeability in creep tests, in wet conditions (see Example 3).
Figure 2A:
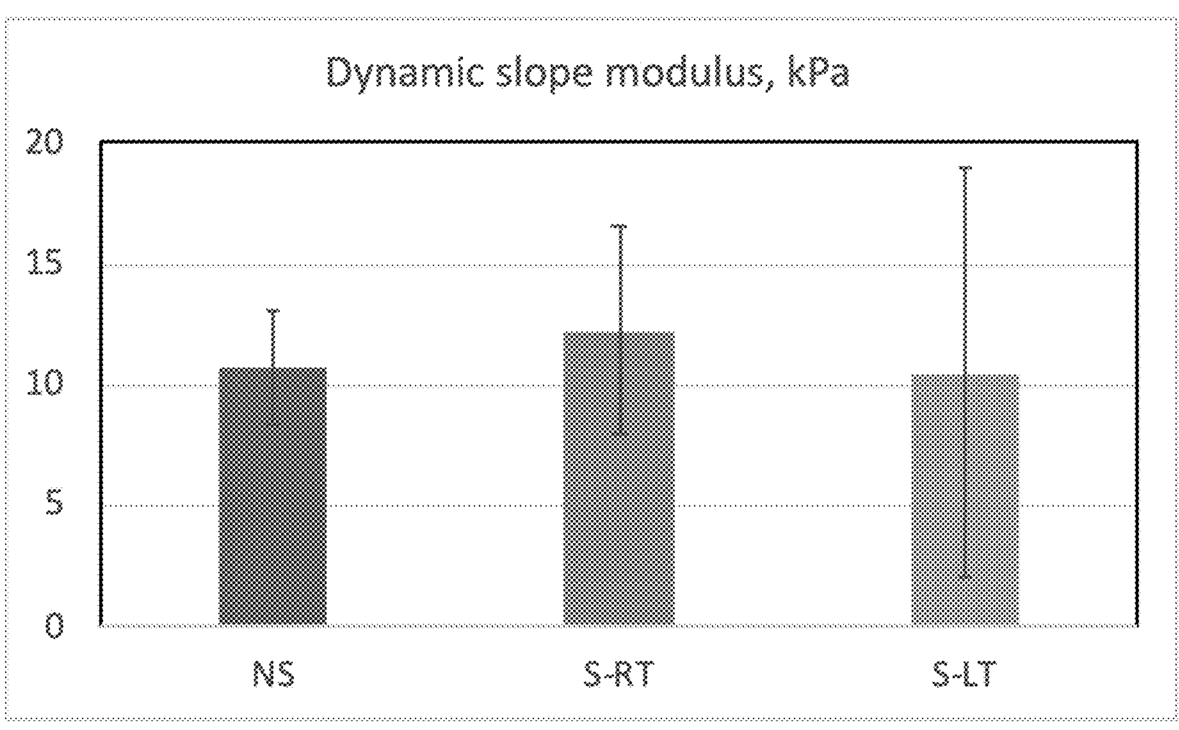
FIG. 2A. Dynamic slope moduli for dynamic strain sweep tests, in wet conditions (see Example 3).
Figure 2B:
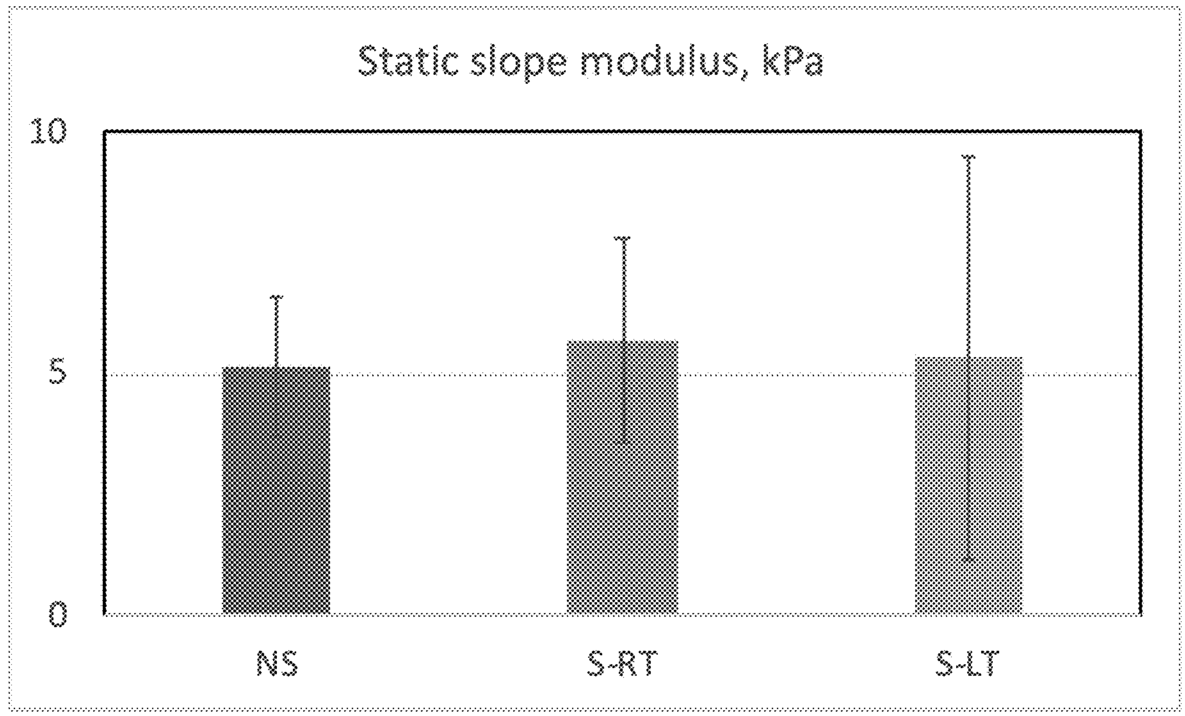
FIG. 2B. Static slope moduli for dynamic strain sweep tests, in wet conditions (see Example 3).

As seen from FIG. 1A-C, in creep tests there are significant differences in some properties values between some sample types but not others (error bars=standard deviation in wet conditions). For example, S-RT samples have lower modulus in creep and higher permeability in creep vs. S-LT samples. Hence, there is an effect of temperature control (lowered temperature) during sterilization procedure.

TABLE 4

| Wet conditions (mean values) | | | |
|---|---|---|---|
| | NS | S-RT | S-LT |
| Invariant modulus, in creep, kPa | 48 | 45 | 68 |
| Invariant memory value, in creep | 0.042 | 0.06 | 0.55 |
| Permeability, in creep, mDarcy | 0.98 | 1.65 | 1.0 |
| Dynamic slope modulus, kPa | 10.5 | 12 | 10.0 |
| Static slope modulus, kPa | 5 | 6 | 5 |

In dynamic wet conditions (FIG. 2A-B) at 25° C. at 1 Hz there were no significant differences between dynamic and static stress/strain ratios (slope moduli) between the samples (NS, S-RT and S-LT).

Figure 3:
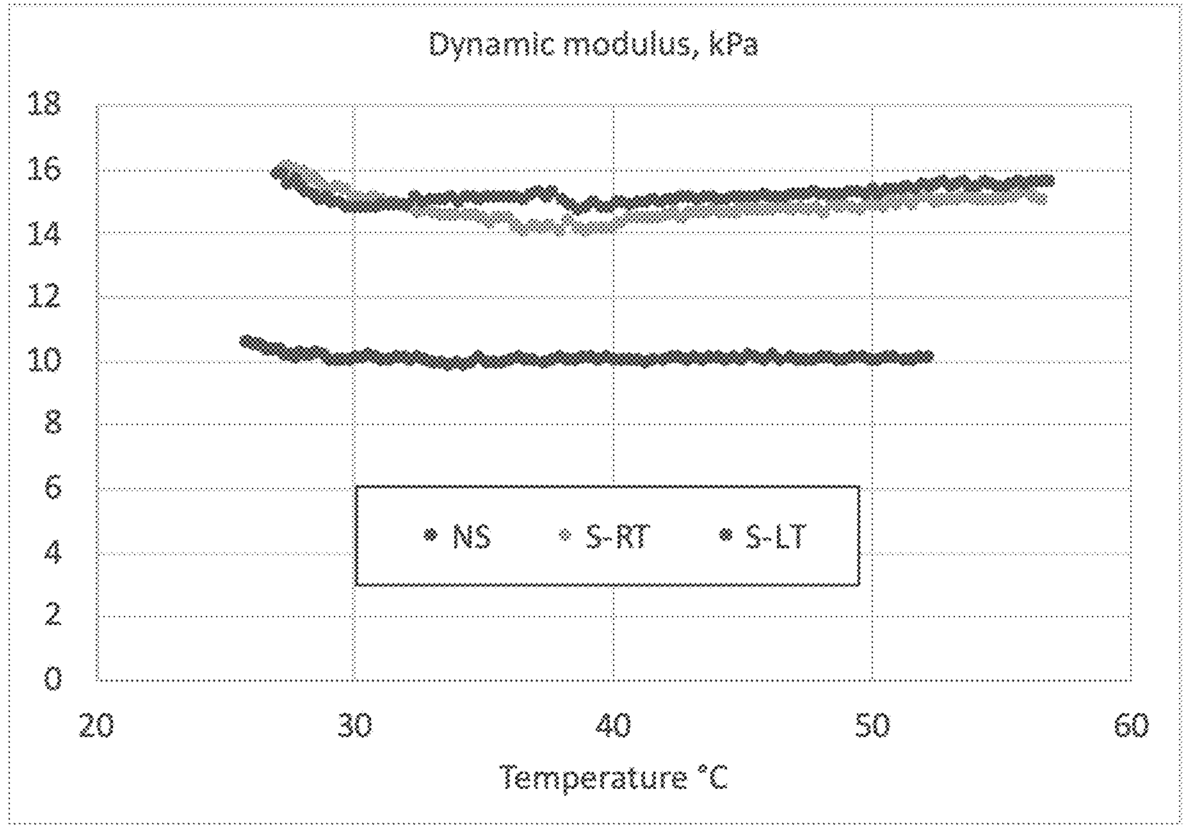
FIG. 3. Dynamic modulus vs. test temperature in dry conditions. As seen, there are no effect of temperature on the modulus values, but there are statistically significant (p=0.00) differences between non-sterilized and sterilized samples (see Example 3).

Surprisingly, in dynamic dry conditions at 1 Hz with temperature rise till 60° C., there were significant differences, p=0.00 (when confidence interval is 95%, the values $p<0.05$ are statistically significant for two-sided permutation t-test), between samples in dynamic and static stress/strain ratios, indicating that the S-RT and S-LT scaffolds become stiffer after the sterilization process (FIG. 3). These differences were between non-sterile (NS) and sterile samples (S-RT & S-LT), but not between those sterilized in RT (S-RT) or in lowered temperature (S-LT). The change in temperature during dynamic testing had no effect on the properties until the 60° C. Also, there seem to be no effect of the test temperature on samples stiffness (i.e. the stress/strain ratio of a material) until 60° C., so it can be concluded the differences observed are mainly due to the sterilization process, and that different temperatures; room temperature (S-RT) or lower (S-LT) does not have an effect on these samples' properties.

These results indicate that the sterilization (in RT or in lower temperature (LT)) in general stabilizes the scaffold properties, which is only clearly visible in these tests in dry state.

As seen in FIG. 3 and Table 5, there are no effect of temperature on the modulus values, but there is statistically significant (p=0.00) difference between non-sterilized and sterilized scaffolds.

TABLE 5

| Dry conditions (mean values) | | | |
|---|---|---|---|
| | NS | S-RT | S-LT |
| Dynamic modulus, kPa | 10 | 14-16 | 14-16 |

Generally, sterilization has been thought to have inferior effects on material properties of scaffolds, but in this case the sterilization leads to an unexpected result: gamma-radiation seems to have a positive effect of stabilizing the biomechanical properties of the scaffolds.

In summary this Example 3 demonstrates the following effect of the sterilization procedure on the materials vs. non-sterile materials (the changes are thus either Poor—that change of the property was not desirable, Fair—neutral effect, no statistically significant difference, or Good—the change of the property was desirable):

| Properties | Its increase is desirable? | S-RT vs. NS | S-LT vs. NS |
|---|---|---|---|
| Invariant creep modulus (wet conditions) | Yes | No changes | Increases |
| Higher values help bearing the static load | | (Fair) | (Good) |
| Permeability in creep (wet conditions) | No | Increases | No changes |
| Lower values help keeping synovial fluid in static | | (Poor) | (Good) |
| Dynamic modulus (wet conditions) | No | No changes (Fair) | |
| Lower values improve compliance | | | |
| Dynamic modulus (dry conditions) Higher values with temperature indicate stability of the material structure | Yes | Increases (Good) | |
| Dynamic modulus vs. temperature (dry conditions) | Yes | No changes (Fair) | |

As mentioned herein before, a desired improvement means i) an increase in one or more biomechanical parameters or biomechanical features, ii) a decrease in one or more biomechanical parameters or biomechanical features, or iii) no change in one or more biomechanical parameters or biomechanical features.

As seen from the table above, an increase is desirable for the following biomechanical parameters: Invariant creep modulus (wet conditions), dynamic modulus (dry conditions), and dynamic modulus vs. temperature (dry conditions), whereas a decrease or no change is desired for the following biomechanical parameters: Permeability in creep (wet conditions) and dynamic modulus (wet conditions).

As mentioned herein before, a desired improvement is when an increase (or decrease) is 1% or more, 2% or more, 3% or more, 4% or more, 5% or more, 6% or more, 7% or more, 8% or more, 9% or more or 10% or more; or when no change is less than 10%, less than 9%, less than 8%, less than 7%, less than 6%, less than 5%, less than 4%, less than 3%, less than 2% or less than 1%.

Therefore, it can be assumed that the sterilization procedure of gamma irradiation in RT or in lower temperature (LT) is a positive step for these kinds of scaffolds to achieve more stable structure in both, dry as well as in wet state in dynamics. As well, sterilization in lowered temperature leads to preferable results compared to sterilization in RT, shown especially in wet creep conditions.

It was also confirmed that the rhCo-PLA scaffold as described in Example 1 has unexcepted reactivity toward gamma-sterilization conditions (dose and temperature control), such as improved biomechanical stability, allowing more precise control of mechanical properties and needed optimization of the materials vs. clinical demands. This effect was unexpected as it is generally known that the irradiation weakens or even destroys many organic materials and polymers.

The invention claimed is:

1. A method for preparing a sterilized scaffold for medical use, the method comprising the steps of:

i) Loading collagen to a fiber mesh containing fibers of PLA to obtain a PLA-collagen scaffold, ii) Drying the PLA-collagen scaffold obtained from step i), and iii) Sterilizing the PLA-collagen scaffold obtained from the drying step ii) via gamma irradiation to obtain the sterilized scaffold.

2. A method according to claim 1, wherein the sterilized scaffold obtained has improved biomechanical properties compared with an unsterilized scaffold, and wherein the improved biomechanical properties are expressed as an increase in one or more biomechanical parameters or biomechanical features, wherein the one or more biomechanical parameters or biomechanical features is selected from invariant creep modulus, when tested under wet conditions, and dynamic modulus, when tested under dry conditions.

3. A method according to claim 1, wherein the sterilized scaffold obtained has improved biomechanical properties compared with an unsterilized scaffold, and wherein the improved biomechanical properties are expressed as a decrease or a change of 10% or less in one or more biomechanical parameters or biomechanical features, wherein the biomechanical parameters or biomechanical features are selected from permeability in creep and dynamic modulus, both tested under wet conditions.

4. A method according to claim 2, wherein the increase is 1% or more, 2% or more, 3% or more, 4% or more, 5% or more, 6% or more, 7% or more, 8% or more, 9% or more or 10% or more.

5. A method according to claim 3, wherein the change is less than 10%, less than 9%, less than 8%, less than 7%, less than 6%, less than 5%, less than 4%, less than 3%, less than 2% or less than 1%.

6. A method according to claim 1, wherein the temperature of the PLA-collagen scaffold before sterilizing is essentially the same or higher than the temperature of the PLA-collagen scaffold during sterilizing.

7. A method according to claim 1, wherein the sterilization is carried out at a temperature in a range of from −200° C. to 40° C.

8. A method according to claim 1, wherein the gamma irradiation dose is at the most 25 kGy.

9. A method according to claim 1, wherein the loading in step i) is performed with a gel of collagen.

10. A method according to claim 9, wherein the concentration of the collagen in the gel is from about 0.1% to 2.0% w/w.

11. A method according to claim 1, wherein the scaffold obtained in step i) contains from 5 to 25% w/w collagen, the percentage being based on the total amount of PLA and collagen.

12. A method according to claim 1, wherein the collagen is recombinant collagen, tissue derived collagen, or combinations thereof.

13. A method according to claim 1, wherein the mesh containing fibers of PLA and used in step i) is obtained by i) providing PLA in solid form ii) subjecting PLA to a process whereby fibers of PLA are obtained, and iii) subjecting the obtained fibers to a process, whereby a mesh of fibers is obtained.

14. A method according to claim 13, wherein step ii) is performed by spinning.

15. A method according to claim 13, wherein the mesh in step iii) of claim 13 is subjected to a process comprising carding or needle punching to obtain a 3D network.

16. A method according to claim 1, wherein PLA is a polylactide.

17. A method according to claim 1, wherein a further step of crosslinking is performed before sterilization.

18. A method according to claim 17, wherein the collagen in the PLA-collagen is crosslinked.

19. A method according to claim 3, wherein the decrease is 1% or more, 2% or more, 3% or more, 4% or more, 5% or more, 6% or more, 7% or more, 8% or more, 9% or more or 10% or more.

* * * * *